(12) United States Patent
Arnold

(10) Patent No.: US 7,292,721 B2
(45) Date of Patent: *Nov. 6, 2007

(54) CALIBRATION OF TISSUE DENSITIES IN COMPUTERIZED TOMOGRAPHY

(76) Inventor: Ben A. Arnold, 1385 Burkesville Rd., Columbia, KY (US) 42728

( * ) Notice: Subject to any disclaimer, the term of this patent is extended or adjusted under 35 U.S.C. 154(b) by 0 days.

This patent is subject to a terminal disclaimer.

(21) Appl. No.: 11/296,936

(22) Filed: Dec. 8, 2005

(65) Prior Publication Data

US 2006/0088198 A1    Apr. 27, 2006

Related U.S. Application Data

(63) Continuation of application No. 09/989,995, filed on Nov. 21, 2001, now Pat. No. 6,990,222.

(51) Int. Cl.
*G06K 9/00* (2006.01)

(52) U.S. Cl. .................. 382/131; 378/18; 378/207; 600/331; 250/252.1

(58) Field of Classification Search ................ 382/128, 382/129, 130, 131, 132, 133, 134; 378/18, 378/207; 600/183, 313, 331, 338, 343, 358, 600/425, 442, 534, 562, 334; 604/22, 268, 604/274; 607/50, 51, 149; 250/363.04, 250/252.1, 339.09, 341.5, 559.1
See application file for complete search history.

(56) References Cited

U.S. PATENT DOCUMENTS

| | | | |
|---|---|---|---|
| 2,399,650 A | 5/1946 | Moyer |
| 2,426,884 A | 9/1947 | Kieffer |
| 3,705,383 A | 12/1972 | Frayer |
| 3,944,830 A | 3/1976 | Dissing |
| 4,115,691 A | 9/1978 | Oldendorf |
| 4,115,762 A | 9/1978 | Akiyama et al. |
| 4,124,799 A | 11/1978 | Schittenhelm |
| 4,233,507 A | 11/1980 | Volz |
| 4,400,827 A | 8/1983 | Spears |

(Continued)

FOREIGN PATENT DOCUMENTS

EP    0 253 742 A1    1/1998

(Continued)

OTHER PUBLICATIONS

Agatston, Arthur S., et al. *Quantification of coronary artery calcium using ultrafast computed tomography*, American College of Cardiology, 1990; 15: pp. 827-832.

(Continued)

*Primary Examiner*—Samir Ahmed
*Assistant Examiner*—Abolfazl Tabatabai
(74) *Attorney, Agent, or Firm*—Jerry Turner Sewell

(57) ABSTRACT

A hybrid calibration method uses a calibration phantom (exterior reference) scanned simultaneously with the patient, and one or more known tissues of the subject (interior reference) to create a hybrid calibration reference that improves the measurement of tissue densities throughout the body. In addition, the calibration method is used to quantitatively define boundaries of tissue and organs for more accurate measurements of lengths, areas and volumes. Another aspect of the invention uses the calibrated images to quantitatively preset absolute window/levels for filming and image display, which provides standardized viewing for diagnostic purposes.

25 Claims, 8 Drawing Sheets

U.S. PATENT DOCUMENTS

| | | |
|---|---|---|
| 4,475,122 A | 10/1984 | Green |
| 4,593,400 A | 6/1986 | Mouyen |
| 4,593,406 A | 6/1986 | Stone |
| 4,649,561 A | 3/1987 | Arnold |
| 4,721,112 A | 1/1988 | Hirano et al. |
| 4,724,110 A | 2/1988 | Arnold |
| 4,779,621 A | 10/1988 | Mattson |
| 4,811,373 A | 3/1989 | Stein |
| 4,829,549 A | 5/1989 | Vogel et al. |
| 4,852,137 A | 7/1989 | Mackay |
| 4,922,915 A | 5/1990 | Arnold et al. |
| 4,941,164 A | 7/1990 | Schuller et al. |
| 4,947,414 A | 8/1990 | Stein |
| 4,985,906 A | 1/1991 | Arnold |
| 5,005,196 A | 4/1991 | Lanza et al. |
| 5,034,969 A | 7/1991 | Ozaki |
| 5,040,199 A | 8/1991 | Stein |
| 5,049,746 A | 9/1991 | Ito |
| 5,056,130 A | 10/1991 | Engel |
| 5,068,788 A | 11/1991 | Goodenough et al. |
| 5,122,664 A | 6/1992 | Ito et al. |
| 5,123,037 A | 6/1992 | Picard et al. |
| 5,132,995 A | 7/1992 | Stein |
| 5,138,553 A | 8/1992 | Lanza et al. |
| 5,148,455 A | 9/1992 | Stein |
| 5,150,394 A | 9/1992 | Karellas |
| 5,187,731 A | 2/1993 | Shimura |
| 5,247,559 A | 9/1993 | Ohtsuchi et al. |
| 5,335,260 A | 8/1994 | Arnold |
| 5,365,564 A | 11/1994 | Yashida et al. |
| 5,402,785 A | 4/1995 | Leigh et al. |
| 5,415,176 A | 5/1995 | Sato et al. |
| 5,465,284 A | 11/1995 | Karellas |
| 5,521,955 A | 5/1996 | Gohno et al. |
| 5,528,644 A | 6/1996 | Ogawa et al. |
| 5,568,811 A | 10/1996 | Olstad |
| 5,577,089 A | 11/1996 | Mazess |
| 5,594,775 A | 1/1997 | Hangartner |
| 5,696,805 A | 12/1997 | Gaborski et al. |
| 5,712,892 A | 1/1998 | Weil et al. |
| 5,757,877 A | 5/1998 | Wilting |
| 5,774,519 A | 6/1998 | Lindstrom et al. |
| 5,852,647 A | 12/1998 | Schick et al. |
| 5,870,697 A | 2/1999 | Chandler et al. |
| 5,891,030 A | 4/1999 | Johnson et al. |
| 5,949,842 A | 9/1999 | Schafer et al. |
| 5,953,444 A | 9/1999 | Joseph et al. |
| 6,026,142 A | 2/2000 | Gueziec et al. |
| 6,052,477 A | 4/2000 | Wang et al. |
| 6,127,669 A | 10/2000 | Sidiropoulos et al. |
| 6,226,350 B1 | 5/2001 | Hsieh |
| 6,233,304 B1 | 5/2001 | Hu et al. |
| 6,243,437 B1 | 6/2001 | Hu et al. |
| 6,246,784 B1 | 6/2001 | Summers et al. |
| 6,249,692 B1 | 6/2001 | Cowin |
| 6,278,761 B1 | 8/2001 | Kim et al. |
| 6,301,495 B1 | 10/2001 | Gueziec et al. |
| 6,320,931 B1 | 11/2001 | Arnold |
| 6,372,264 B1 | 4/2002 | Dixon |
| 6,421,552 B1 | 7/2002 | Hsieh |
| 6,490,476 B1 | 12/2002 | Townsend et al. |
| 6,605,274 B1 | 8/2003 | Dillmann et al. |
| 6,639,965 B1 | 10/2003 | Hsieh et al. |
| 6,674,834 B1 | 1/2004 | Acharya et al. |
| 6,687,333 B2 | 2/2004 | Carroll et al. |
| 6,697,451 B2 | 2/2004 | Acharya et al. |
| 6,792,074 B2 | 9/2004 | Erbel et al. |
| 2003/0095695 A1 | 5/2003 | Arnold |

FOREIGN PATENT DOCUMENTS

EP            1 092 392 A2     10/2000

OTHER PUBLICATIONS

Baldy, R.E., et al., A Fully-Automated Computer Assisted Method of CT Brain Scan Analysis for the Measurement of Cerebrospinal Fluid Spaces and Brian Absorption Density, *Neuroradiology*, vol. 28, 1986, pp. 109-117.

PCT/US 02/37765, ISR dated Oct. 21, 2003, Nov. 23, 2002, Image Analysis, Inc.

PCT/US02/37247, ISR dated Jul. 9, 2003, Jun. 5, 2003, Image Analysis, Inc.

Bhattacharya, P., et al., One-page abstract, A new edge detector for gray volumetric data, *Comput. Biol. Med.*, vol. 26, No. 4, Jul. 1996, pp. 315-328.

Borkan, Gary A., et al., Assessment of abdominal fat content by computed tomography, *Am. J. Clin. Nutr.*, Jul. 1982, pp. 172-177.

Brown, Matthew S., et al., Knowledge-based segmentation of thoracic computed tomography images for assessment of split lung function, *Medical Physics*, vol. 27, No. 3, Mar. 2000, pp. 592-598.

Cann, Christopher E., Ph.D., Low Dose CT Scanning for Quantitative Spinal Mineral Analysis, *Radiology*, vol. 140, No. 3, Sep. 1981, pp. 813-815.

Cann, Christopher E., et al., Precise Measurement of Vertebral Mineral Content Using Computed Tomography, *Journal of Computer Assisted Tomography*, vol. 4, No. 4, Aug. 1980, pp. 493-500.

Cann, Christopher E., et al., Spinal Mineral Loss in Oophorectomized Women, *Journal of the American Medical Association*, vol. 244, No. 18, Nov. 7, 1980, pp. 2056-2059.

Chuang, K.S., et al., One-page abstract, Evaluation of inherent gray-level dynamic range in a digital image using the runs test and join-count statistics, *Medical Physics*, vol. 20, No. 5, Jan.-Feb. 1993, pp. 39-45.

COMPUMED, Copy of Brochure, *Bone Mineral Density Evaluation*, five pages.

Cosman, F., et al., Radiographic Absorptiometry; A Simple Method for Determination of Bone Mass, *Osteoporosis International*, 1991, pp. 34-38.

Detrano, Robert, et al., Accurate coronary calcium phosphate mass measurements from electron beam computed tomograms, *American Journal of Cardiac Imaging*, vol. 9, No. 3, Jul. 1995, pp. 167-173.

Di Giandomenico, E., et al., One-page abstract, Quantitative evaluation of blood in vivo with computed tomography, *Radiol. Med (Torino)*, (Article in Italian), vol. 85, No. 4, Apr. 1993, pp. 416-420.

Dougherty, Geoffrey, et al., Measurement of thickness and density of thin structures by computed tomography: A simulation study, *Medical Physics*, vol. 26, No. 7, Jul. 1999, pp. 1341-1348.

General Electric, Marketing Materials distributed in 1987, four pages.

Grashuis, J.L., et al., Semi-Automatic Contour Detection in CT-Scans of the Lumbar Spine, *Proceedings of the Sixth International Workshop on Bone and Soft Tissue Densitometry*, Buxton, England, Sep. 22-25, 1987, p. 33.

Grauer, Walter O., et al., Quantification of body fat distribution in the abdomen using computed tomography, *Am. J. Clin. Nutr.*, 1984; 39: pp. 631-637.

Greaser, L.E., 3rd et al., One-page abstract, Electron-beam CT: the effect of using a correction function on coronary artery calcium quantitation, *Acad. Radiol.*, vol. 6, No. 1, Jan. 1999, pp. 40-48.

Hawkes, D.J., et al., Development of a Digital Radiographic Technique to Measure Bone Mineral in Neonates, *Transactions of the Fifth International Workshop on Bone and Soft Tissue Densitometry Using Computed Tomography*, The University of Pennsylvania, Oct. 14-18, 1985, p. 76.

Hayashi, Y, Diagnosis of Osteoporosis and Assessment of Bone Mass by Radiography: The Most Convenient Procedure to Reduce the Risk of Fracture, *Osteoporosis International*, Suppl. 1, 1993, pp. 78-80.

Heil, Robert H., Jr., et al. Quantitative Materials Evaluation and Inspection with the Image Analyzing Computer, *Proceedings of the Society of Photo-Optical Instrumentation Engineers*, Feb. 1972, pp. 131-143

Hermann, K-P, et al., Muscle- and Fat-equivalent Polyethylene-based Phantom Materials for X-ray Dosimetry At Tube Voltages Below 100 kV, *Phys. Med. Biol.*, vol. 31, No. 9, 1986, pp. 1041-1046.

Hermann, K-P, et al., Polyethylene-based Water-equivalent Phantom Material for X-ray Dosimetry at Tube Voltages from 10 to 100kV, *Phys. Med. Biol.*, vol. 30, No. 11, 1985, pp. 1195-1200.

Heuck, F.H.W., Quantitative Measurements of Mineral Content in Bone Disease, *Symposium Ossium*, Session 10, E.G. Livingstone, Edingburgh, Scotland, 1970, pp. 141-147.

Hsieh, Jiang, et al., An iterative approach to the beam hardening correction in cone beam CT, *Medical Physics*, vol. 27, No. 1, Jan. 2000, pp. 23-29.

Hubener, K.H., et al., One-page abstract, Computer tomographic densitometry of human blood. The effect of absorption by parenchymatous organs and effusions (author's transl)., *ROFO Fortschr Geb Rontgenstr Nuklearmed*, (Article in German), vol. 130, No. 2, Feb. 1979, pp. 185-188.

Kalender, W.A., et al., Methodological Aspects of Bone Mineral Measurements by QCT: Minimizing Operator Influence on Reproducibility, *Proceedings of the Sixth International Workshop on bone and Soft Tissue Densitometry*, Buxton, England, Sep. 22-25, 1987, p. 31.

Kalender, Willi A., et al., Vertebral Bone Mineral Analysis: An Integrated Approach with CT, *Radiology*, 1987, vol. 164, No. 2, Aug. 1987. pp. 419-423.

Keller, James M., et al., Automatic Outlining of Regions on CT Scans, *Journal of Computer Assisted Tomography*, vol. 5, No. 2, Apr. 1981, pp. 240-245.

Kemerink, G.J., et al., One-page abstract, Scanner conformity in CT densitometry of the lungs, *Radiology*, vol. 197, No. 3, Dec. 1995, pp. 749-752.

Kruger, Robert A., et al., Dual Energy Film Subtraction Technique for Detecting Calcification in Solitary Pulmonary Nodules, *Radiation Physics*, vol. 140, Jul. 1981, pp. 213-219.

Kvist, Henry, et al., Total and visceral adipose-tissue volumes derived from measurements with computed tomography in adult men and women: predictive equations, *Am. J. Clin. Nutr.*, 1998, pp. 1351-1361.

Levi, Clifford, et al., The Unreliability of CT Numbers as Absolute Values, *AJR:139*, Sep. 1982, pp. 443-447.

McCullough, Cynthia H., Ph.D., Electron-Beam CT: Use of a Calibration Phantom to Reduce Variability in Calcium Quntitation, Departments of Diagnostic Radiology and Physiology and Biophysics, Mayo Clinic and Mayo Foundation, Rochester, Minnesota, Radiology 1995, vol. 196, No. 1, Jul. 1995, pp. 159-165.

Megnien, J.L., et al, Coronary calcification and Its relation to extracoronary atherosclerosis in asymptomatic hypercholesterolemic men, circulation, vol. 85, 1992; pp. 1799-1807.

Reed, Judd E., et al., System for Quantitative Analysis of Coronary Calcification via Electron Beam Computed Tomography, *Medical Imaging 1994, Physiology and Function from Multidimensional Images, SPIE*, vol. 2168, Feb. 13-14, 1994, pp. 43-53.

Schmitt, W.G., et al., One-page abstract, Attenuation values of normal and pathological liver tissue as a basis for computer tomographic densitometry of fatty livers (author's transl.), *ROFO Fortschr Geb Rontgenstr Nuklearmed*, (Article in German), vol. 129, No. 5, Nov. 1978, pp. 555-559.

Serpico, S., et al., Evaluation and Standardization in Bone Densitometry, *Transactions of the Fifth International Workshop on Bone and Soft Tissue Densitometry Using Computed Tomography*, The University of Pennsylvania, Oct. 14-18, 1985, p. 75.

Stoel, B.C., et al., One-page abstract, Sources of error in lung densitometry with CT, *Invest. Radiol.*, vol. 34, No. 4, Apr. 1999, pp. 303-309.

Vogel, John Max, Application Principles and Technical Consideration in SPA, *Proceedings Osteoporosis Update*, Harry Jerant ed., Radiology Research and Education Foundation, University of California, 1987, pp. 219-231.

Wankling, P.F., et al., Computer Recognition Applied to C.T. Scans for the Automation of the Procedure for Bone Mineral Measurement Allowing Consistent Measurement Without Operator Intervention, *Proceedings of the Sixth International Workshop on Bone and Soft Tissue Densitometry*, Buxton, England, Sep. 22-25, 1987, p. 32.

Yoon, H.C., et al., One-page abstract, Coronary artery calcium: alternate methods for accurate and reproducible quantitation, *Acad. Radiol.*, vol. 4, No. 10, Oct. 1997, pp. 666-673.

Zamenhof, Robert G., et al., A Theoretical Sensitivty Evaluation of CT for the Measurement of Bone Mineral in Cortical and Vertebral Bone. *Proceedings of CT Densiometry Workshop, Journal of Computer Assisted Tomography*, vol. 3, No. 6, 1979, p. 852.

Zeichner, S.J., et al., Quantitative Digital Subtraction Radiography: A Clinical Method for Bone Mineral Determination, *Transactions of the Fifth International Workshop on Bone and Soft Tissue Densitometry Using Computer Tomography*, The University of Pennsylvania, Oct. 14-18, 1985, one page.

Technical Note, Automatic Outlining Technique for EMI Scanner Pictures, *Medical & Biological Engineering & Computing*, vol. 17, Sep. 1979.

CALIBRATION OF TISSUE DENSITIES IN COMPUTERIZED TOMOGRAPHY

This application is a continuation of U.S. patent application Ser. No. 09/989,995, filed on Nov. 21, 2001 now U.S. Pat. No. 6,990,222, the entirety of which is hereby incorporated herein by reference.

BACKGROUND OF THE INVENTION

1. Field of the Invention

The present invention is in the field of medical imaging using computerized tomography (CT), and in particular, is directed to a method to determine tissue densities in the body of a subject and to provide calibrated display of images.

2. Description of the Related Art

CT scanners have become a major diagnostic modality in modern medicine and are widely used for many types of exams. Most exams are performed by subjective viewing of the cross-sectional images on either film or electronic displays. This subjective viewing makes use of assumed quantitative image pixels, which define boundaries of tissues, organs, or foreign masses, and subjective discrimination of tissue types by density differences. Identification of diagnostic details is fundamentally dependent upon the detection of image detail edges.

Measurements of true tissue densities in the living subject have many diagnostic benefits, in addition, to bone densitometry. Several new and promising measurements include lung nodule density, cardiac calcifications, aortic calcifications, soft plaque, fat measurements, BMI, lung volume and density, liver iron content, and the like. Knowledge of true tissue densities will allow diagnostic analysis of images not currently possible. Absolute change in CT numbers may allow new diagnostic criteria. Emphysema, tissue fat content, calcifications, liver iron build up, and the like could be determined from the calibrated data, thus, adding a new dimension to CT interpretation.

Radiologists routinely make subjective, and even quantitative measurements of foreign masses, tissues or organs by manually placing cursors to define the 2-D extent of the target. If the window and/or level (brightness and contrast) are changed in the display, the apparent size of the target changes because the boundary is not discrete and is moved in or out of the display range. The measured object size is, thus, frequently inaccurate, and will vary from operator to operator and from scanner to scanner depending on the display conditions and scanner properties.

CT images are filmed by a technologist or other operator and are recorded on standard x-ray film for light box viewing. The size, and apparent density of target objects, and foreign masses depend on the window and level settings. The window/level settings are subjectively set for filming and display of a particular image. In addition, the process to set and adjust the window and level requires operator time and is currently very inefficient. Electronic image data are frequently erased, and only the films retained for the medical records. Later viewing is limited to the subjective display and/or the filming levels previously chosen by the operator.

The foregoing discussion is based on the assumption that pixels and/or voxels of the image are a representation of the true underlying density of the target tissue. Although this assumption is roughly maintained due to the scanner being calibrated to water and air, it is sufficiently inaccurate that many quantitative measurements cannot be made with even the best modern scanners.

There has been significant, recent interest in quantifying coronary calcium, as well as calcifications in the aorta, lungs, breast, and carotids. It is desirable to provide improved calibration methods for all the tissues of the body. Whole body CT scanning is growing rapidly in use. The entire torso is scanned creating many thin slices for analysis and viewing. The radiologist attempts to subjectively analyze many structures from many images, which is laborious and very time consuming. Measurements of densities and volumes of many organs are of interest, including heart, lung, liver, kidneys, prostate, thyroid, pancreas, and the like. Quantitative measurements of calcifications, of areas and volumes, as well as standardized viewing and filming of images, all require improved calibration methods.

CT scanners have been used as quantitative instruments for bone density measurements in quantitative computerized tomography (QCT) by the use of calibration phantoms. More recently, fast CT scanners, such as the Imatron EBCT and GE Light Speed, have been used for coronary calcium analysis with or without phantom calibration. Several calibration approaches have been used in QCT bone densitometry including simultaneous phantom calibration with bone and tissue equivalent phantoms, non-simultaneous calibration with more anthropomorphic phantoms, non-phantom calibration using histogram analysis of fat and muscle regions, simultaneous phantom calibration with blood sample corrections, and dual energy calibration to correct for vertebral fat in bone density measurements. These approaches have been developed specifically for and used for QCT bone densitometry of vertebral trabecular bone.

CT numbers, (Hounsfield Units, HU), are estimates of the attenuation coefficients of tissue relative to water as the calibration reference material. However, CT numbers fail to be truly quantitative for several reasons. For example, the tissue attenuation coefficients are photon energy dependent, and the x-ray beam energy spectra are not measured or known for individual patients. Further, there exists many beam energy spectra in each CT slice, i.e., a unique spectrum for each path length through the patient, and seen at a particular detector element, and a unique spectrum for each view through the patient. The beam spectrum changes with the thickness and composition of tissues in the path length. The quantities of fat, soft tissue, air, and bone vary with each projection. X-ray tube filtration to shape the beam intensity also changes the beam spectrum resulting in variation in CT numbers based on locations within the field of view. Image processing software and current beam hardening corrections have as an objective to improve subjective image quality, and do so, often, at the expense of quantitative information. CT number calibrations and beam hardening corrections are based on idealized phantoms, which are often circular in shape and composed of water, plastics, or other synthetic materials. These differ significantly from the shape and composition of real patients. CT numbers at the edge of the field of view, where a calibration phantom would be placed, are different from those inside the patient. This produces errors in calibration since the phantom can never be placed inside the body cavity. CT numbers vary through the image on each slice, and are dependent on table height, position in the beam, slice thickness, field of view, and sometimes even the time of day as the scanner warms up.

Many diagnoses are based subjectively on perceived tissue densities and regional changes in density as demonstrated by the CT numbers in the image. Results currently are independent of patient variability and CT equipment.

Standardization and calibration of the CT numbers across different patients and CT scanners will aid in interpretation of many conditions.

It is frequently desirable to make quantitative measurements from both two-dimensional (2D) and three-dimensional (3D) data sets in medical imaging. Accurate measurements of organ or tumor volumes and cross-sectional areas of various biological details, such as blood vessels, all have potential medical diagnostic value. Quantification of vascular calcium and micro calcifications throughout the body is valuable in cardiovascular disease and breast cancer detection, for example. All of these tasks use gray scale, voxel-based data. The identification of the edge of a target region may use any of several edge detection algorithms, such as the Sobel operator in either 2D or 3D space. This prior art has used image voxels as outputted from the imaging device, i.e., CT scanner, digital radiography apparatus, magnetic resonant scanner (MRI) or mammography system. In all cases, the image data was not calibrated. Since the image gray scale values vary with the imaging conditions and subject properties, the definition of an edge also varies.

In some cases, the diagnostic detail is defined by a pre-selected threshold value, i.e., if the target element equals or exceeds the threshold value, the detail is counted as a positive diagnostic find. Coronary artery calcifications are a notable example. With currently available CT scanners, calcifications that exceed either 130HU or 90HU are counted as positive finds. The Hounsfield units (HUs) are known to vary with scanner type, x-ray beam energy, reconstruction software, patient size and composition, and the like. As a result, the threshold value varies depending on these conditions. A positive calcification find is thus different for a small female versus a large male. If a patient is scanned on one scanner and scanned later on a second scanner for a follow-up exam, the results will be different. The diagnostic results are therefore dependent upon several variables of the imaging systems, as well as being dependent on the patients.

The use of external calibration phantoms containing bone equivalent samples have been used for some time in QCT Bone Densitometry. Such phantoms have greatly aided the standardization accuracy and reproducibility of bone density measurements. In this case, however, the target tissue, bone, is large, of a high density much larger than soft tissue, and located relatively close to the calibration phantom.

The use of external calibration phantoms has only recently been attempted with coronary calcium quantification. Calibration phantoms have not been used for soft tissue density measurements or for physical dimensional measurements. One of the problems which exists with quantitative CT relates to the variation of image gray scale values throughout the area of the image. The same tissue type located in one location within the body may produce a different Hounsfield unit value versus a different location. That is, the image is not homogeneous throughout. Not only does the image vary in intensity, but it also varies in effective beam energy. As a result, no one unique calibration curve is available for each CT slice or for a complete digital 2D radiograph. The situation is complicated by being dependent upon the position of the object within the scan field, device servicing and calibrations, and x-ray tube wear.

SUMMARY OF THE INVENTION

Unlike prior art devices in which image data was not calibrated, the disclosed invention presents a method to calibrate the image data such that a calibrated image detail edge can be quantitatively defined, located and relocated on follow up images. The reproducibility of physical measurements of target volumes, areas, and distances is greatly improved.

The embodiments of the present invention provide a method to calibrate the image to produce consistent and standardized results, independent of the measurement conditions discussed above (e.g., scanner type, beam energy, reconstruction software, patient size and composition, and the like). Clinical results will be more consistent, more accurate, and more precise. The ability to follow patients on follow-up exams to monitor disease progress will be greatly benefited.

The density differences in Hounsfield unit values between the soft tissues of the body are small, compared to bone density, and they are more difficult to measure. Microcalcifications in the vascular system of the body produce small density differences as well, and are difficult to measure reproducibly. The embodiments of the present invention overcome the small differences in the density of soft tissue or microcalcifications to facilitate measurements throughout the body, both in areas near the external phantom and in areas distant from the external phantom to overcome the inadequacies of the conventional methodology of QCT calibration with an external phantom. In particular, the embodiments of the present invention enable a method to quantify x-ray images that uses a hybrid calibration method that overcomes these limitations.

Filming and viewing CT images can be automated and presented in a quantitative way, which further aids the interpretation. Standardization of filming windows and levels to an absolute scale based on true density provides consistent viewing conditions. Accurate and reproducible filming could be automated and standardized to quantitative values consistent through the medical community.

The body is always in a state of homeostasis, attempting to keep the body in a static and stable condition. Indeed, if some tissues of the body change by even small quantities, life may be challenged. Blood is the fluid of life, and must be maintained within relatively narrow ranges. It is therefore a very consistent substance, both in individual patients, and from patient to patient. The literature on blood composition from the standpoint of effects on physical density shows that blood density and the resulting CT HU values do vary with the hematocrit, red cell volume, iron content, blood fats, and hydration, but these variations are small compared to the required calibration accuracy. This analysis indicates that these variations are acceptable for the disclosed invention. Biologic variations in blood density are expected to generally produce a range of variation of ±2 HU and to rarely exceed ±4 HU.

Since blood is always homogeneously mixed and consistent throughout each individual body, the blood provides for a unique and consistent in vivo calibration tissue. Since blood in the great vessels and heart is centrally located within the body, the position of such blood is ideal as an internal surrogate calibration tissue. The embodiments in accordance with the present invention provide a method that uses blood for tissue calibration in x-ray imaging systems, both when used with an external calibration phantom and when used without an external calibration phantom.

Air calibration is frequently used in CT scanner calibration along with water. The Hounsfield unit value of air is defined as the minimum CT density, usually −1000 HU. Air density is used for quality assurance and routine calibration-file setup of the scanner. Air calibration has not been used as a calibration reference with individual patient scans. It can be assumed that air is a consistent and reproducible substance. Scatter radiation degrades images by adding a DC image component, which reduces image contrast, signal-to-noise ratio, and dynamic range. The measurement of tissue densities and target edges are degraded. The air present within the esophagus provides an internal air reference for calibration in cardiac and chest imaging. Bowel gas provides a potential air reference for the abdomen. The air adjacent, but outside the body in the environment, provides an external air reference. The embodiments in accordance with the present invention provide a method to use both internal air and external air as calibration references in tissue density measurements.

Prior art has disclosed methods to use muscle and visceral fat with histogram analysis to provide calibrations without an external phantom for QCT bone densitometry (See, for example, U.S. Pat. No. 5,068,788 to Goodenough). Muscle and visceral fat always have mixtures of both tissue types, muscle and fat, but the technique proposes that the histogram peaks can be made to represent each tissue type as calibration points. It would be helpful to have a tissue which contains fat without muscle intermixed. This does occur, but, unfortunately on the exterior circumference of the body as subcutaneous fat.

Segmentation techniques are now available to isolate these fat tissues. The thin or not so thin layer of subcutaneous fat can be defined and isolated with modern segmentation techniques. The location of the fat tissue, within the scan field and relative to the target organ, can be measured. Since the fat is distributed around the subject, the fat can be used to make corrections for beam hardening and scatter. The present invention discloses a technique for using subcutaneous fat as a known reference tissue for calibration in tissue density measurements with a CT scanner.

One aspect of the embodiments in accordance with the present invention is a method to calibrate CT images. The method utilizes both an exterior fixed calibration phantom with known samples of tissue equivalent materials, and which also uses an interior sample of tissue of the patient. The exterior calibration phantom has multiple samples of varying densities, varying compositions, or varying densities and varying compositions, which provide a common standard of reference that is consistent for all scanners. The phantom sample readouts provide a regression equation which has a slope that provides a measure of the effective beam energy of the CT scanner for that particular patient. The phantom samples run substantially along the torso of the patient, and the samples are included in each CT slice with simultaneous scanning. The calibration offset, the y-axis intercept, is determined from the patient's own tissue, preferably heart tissue and/or blood. The total heart is segmented in 3D space, and a best representation of the average voxel HU value is determined. Calcifications and fat are removed from the volume by thresholding and by histogram analysis. The calibration makes the assumption that blood density is consistent, and the same for all people. Although blood density does vary with hematocrit, blood cell volume, and iron content, these variations are relatively small and acceptable. Human blood, and heart tissue are remarkably similar in all subjects. In addition, the embodiments of the present invention make use of the assumption that blood is homogeneous and has a constant density in every subject, which allows calibrations using the heart and great vessels.

A hybrid calibration equation is created for each CT slice, and thus each region of the body is calibrated with data from that region. The blood and heart tissue become an additional in vivo phantom sample, which is homogeneous and is dispensed throughout the body. The hybrid calibration is applied to all image pixels of all slices to generate a new data set, which is now calibrated and standardized.

Absolute thresholds and standard edge detection algorithms are applied to the calibrated images to measure volumes, areas, and distances. Organ or tumor mass can be readily measured in a reproducible manner, for example: Absolute and quantitative display ranges, window and level, are set as default values on electronic displays and for filming. Optimum and standardized viewing conditions can be readily maintained for more consistent diagnosis.

The calibration methods disclosed herein can be readily applied on all CT scanners and on all tissues of the body with accurate and reproducible results while reducing operator time. Any tissue in the body can be calibrated including lung, heart, kidney, bone, calcifications, plaque, and the like.

DETAILED DESCRIPTION OF THE PREFERRED EMBODIMENT

Figure 4:
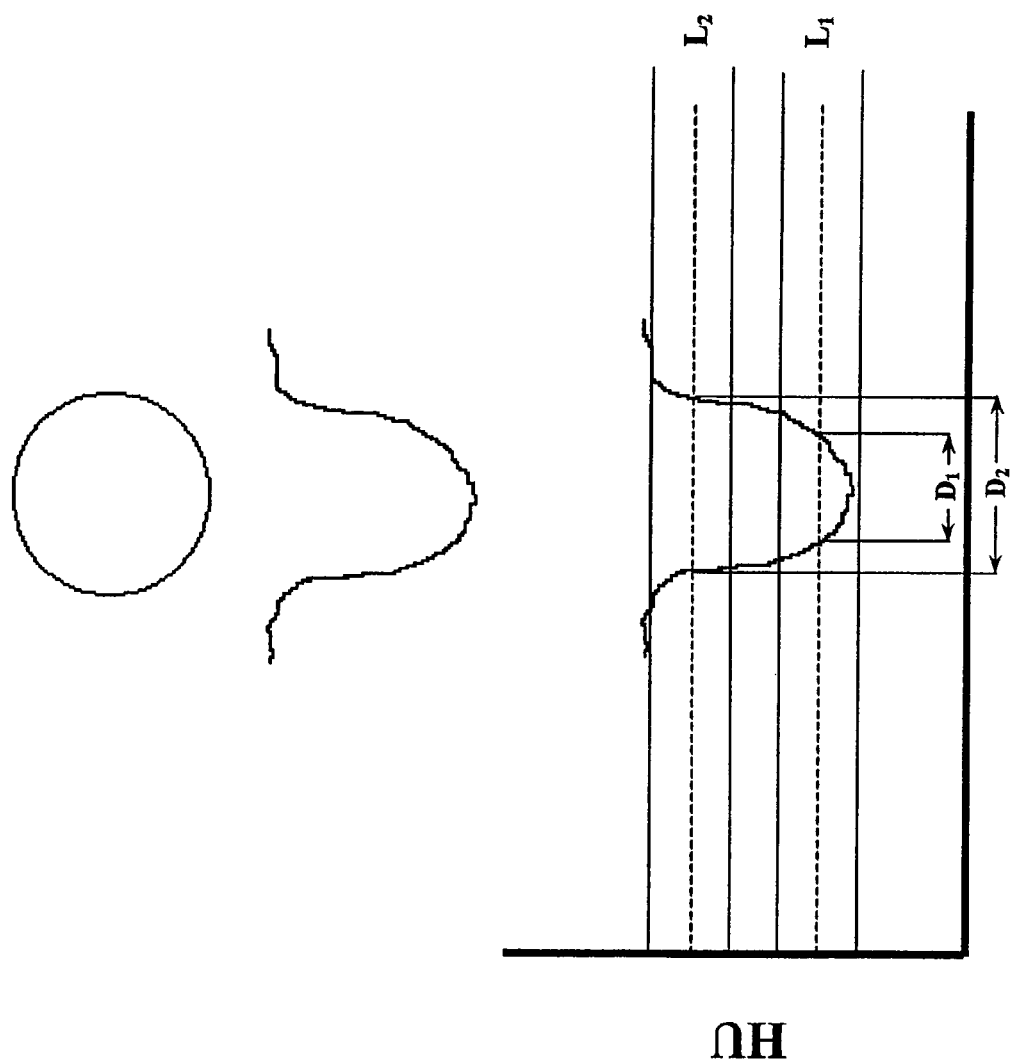
FIG. 4 illustrates the gray scale values at the edges of a tissue detail and the influence of display window and level on the location of the perceived edges and size of the detail.
Figure 5:
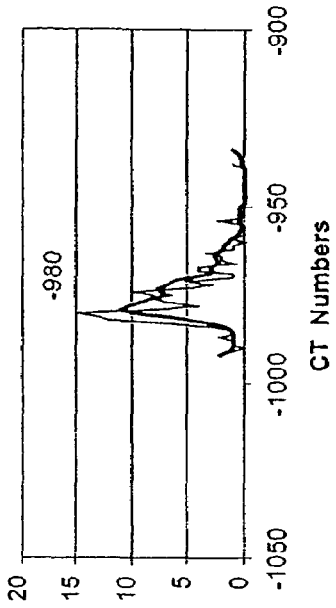
FIG. 5 shows histogram plots of 4 ROIs positioned in air outside and around the body of a patient.
Figure 5:
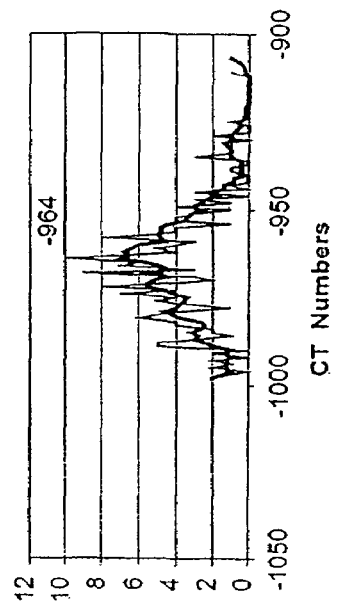
Figure 5:
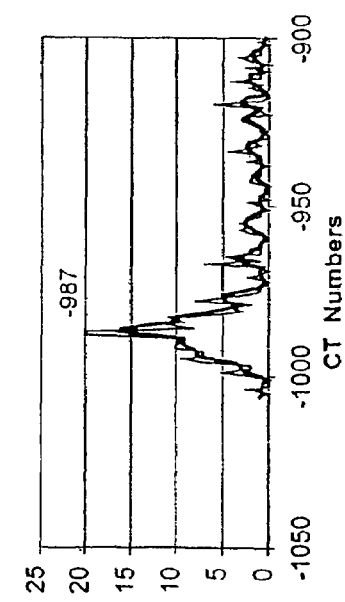
Figure 5:
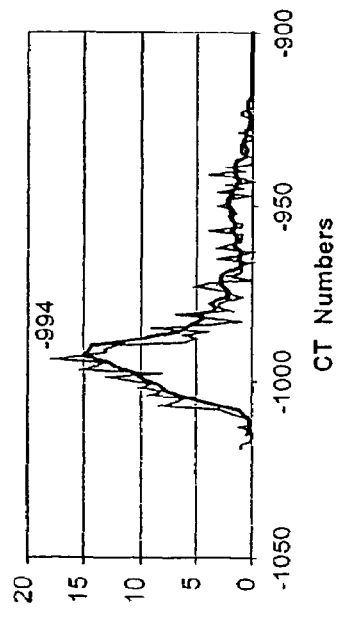

A preferred embodiment of the present invention is described below in connection with the flow chart of FIGS. 6A and 6B in view of the illustrations in FIGS. 1-5.

Figure 6A:
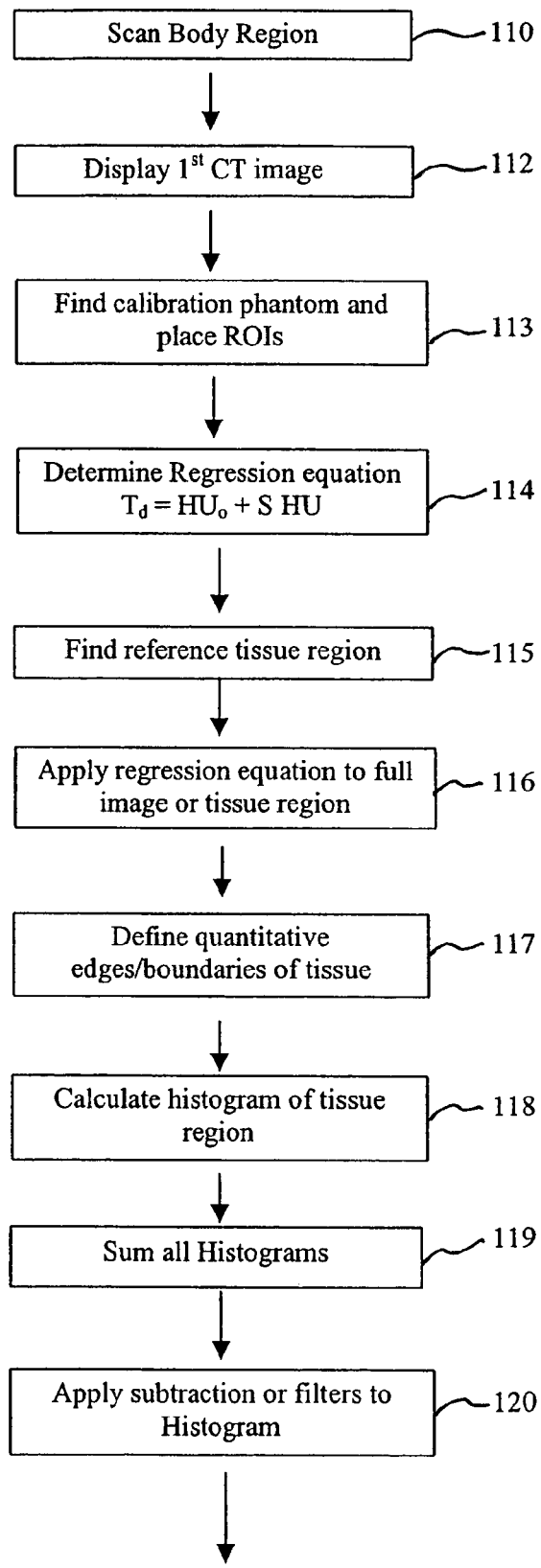
FIGS. 6A and 6B illustrate a flow chart that represents the computational procedure of the hybrid calibration method.
Figure 6B:
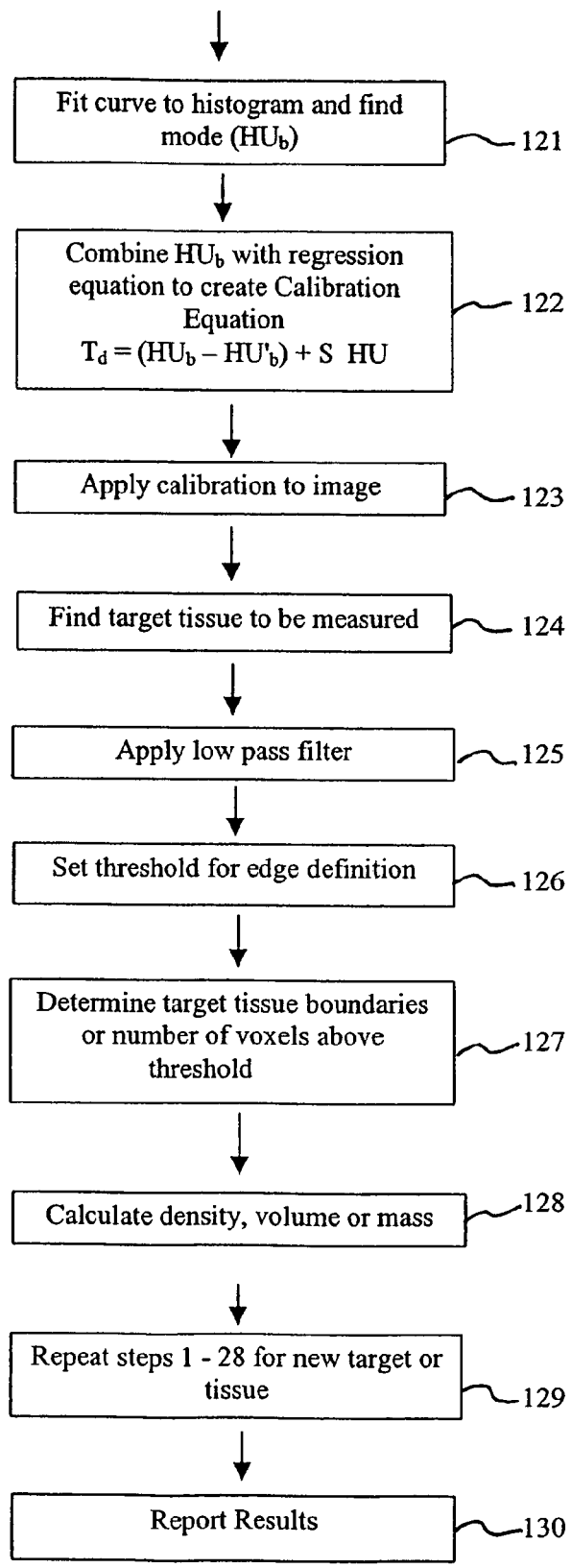

As illustrated by a step 110 in FIG. 6A, a CT scan of the subject is first taken with the subject lying on the reference calibration phantom. Several CT images are taken in a short time period. Preferably, CT images are taken using a multi-slice spiral scan CT scanner or using the EBCT Imatron scanner, although any CT scanner can be used for many tissues. Scans of the heart for coronary calcium analysis will require fast scan times to stop the motion of the beating heart.

Figure 1:
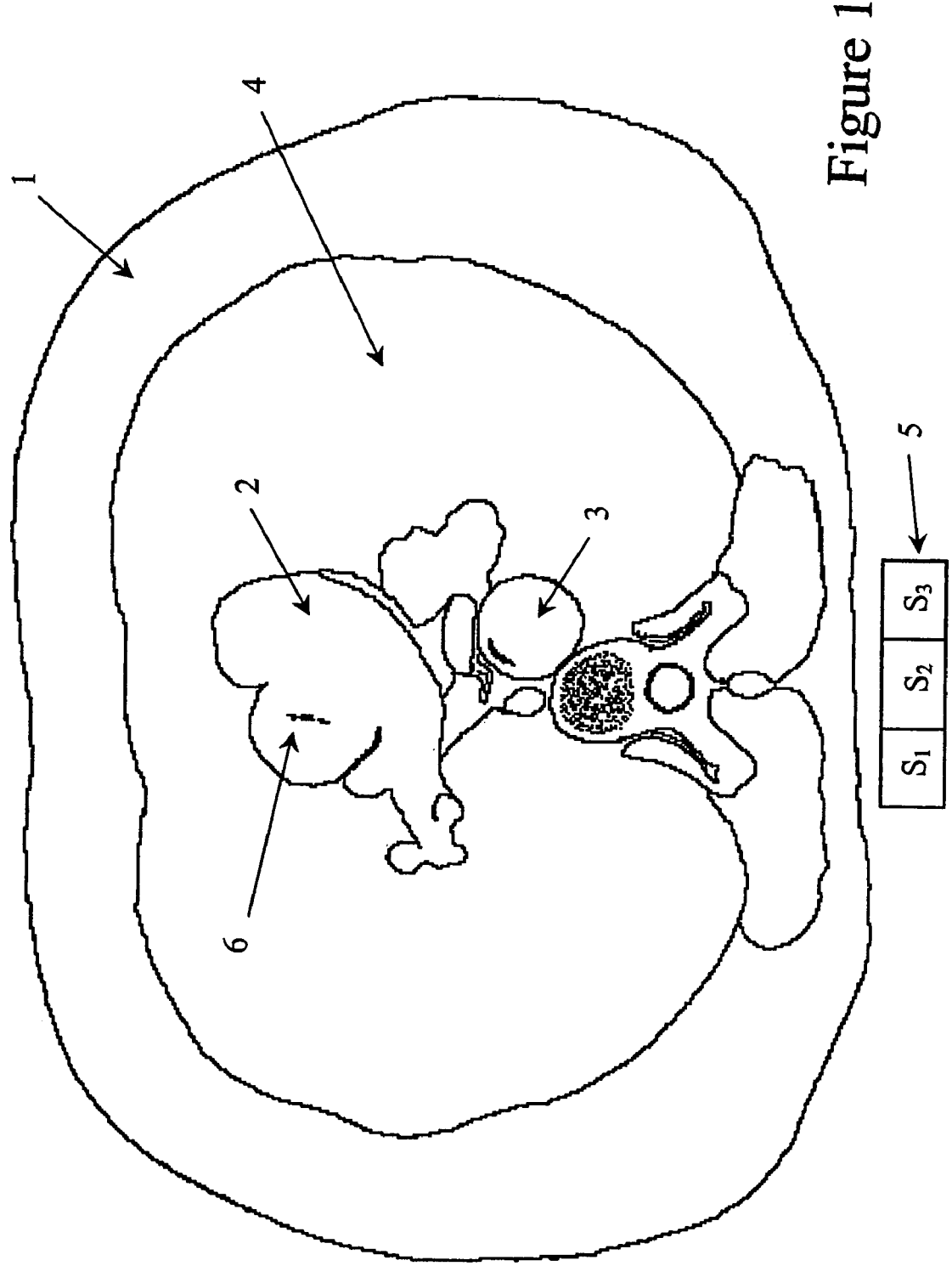
FIG. 1 illustrates a cross-sectional image through the heart with an exterior calibration phantom, in accordance with an embodiment of the present invention.

After reconstruction of the CT images in the scanner computer, a first cross-sectional image of the subject is displayed in a step 112 in FIG. 6A. FIG. 1 illustrates a representative depiction of such an image taken through the heart showing coronary calcium 6. The heart tissue 2, the aorta 3, the lung 4, the chest wall and a reference phantom 5 are shown in FIG. 1. The reference calibration phantom 5 includes three representative samples (S1, S2, and S3) of varying densities. A prior art automated algorithm is used preferably to find the calibration phantom in the image as shown in FIG. 1, and to place Regions-of-Interest (ROIs) within each phantom sample, as illustrated by a step 113 in FIG. 6A. An exemplary prior art algorithm is illustrated in U.S. Pat. No. 4,922,915 to Arnold, which is incorporated by reference herein.

The phantom samples contain known sample densities (Sd) and produce ROI mean CT numbers ($HU_s$) for each sample. For example, sample $S_1$ may preferably contain water density or 0 concentration of the calibration additive material. The calibration additive material is advantageously a calcium containing material such as calcium hydroxyapatite in a solid water equivalent synthetic material.

Figure 2:
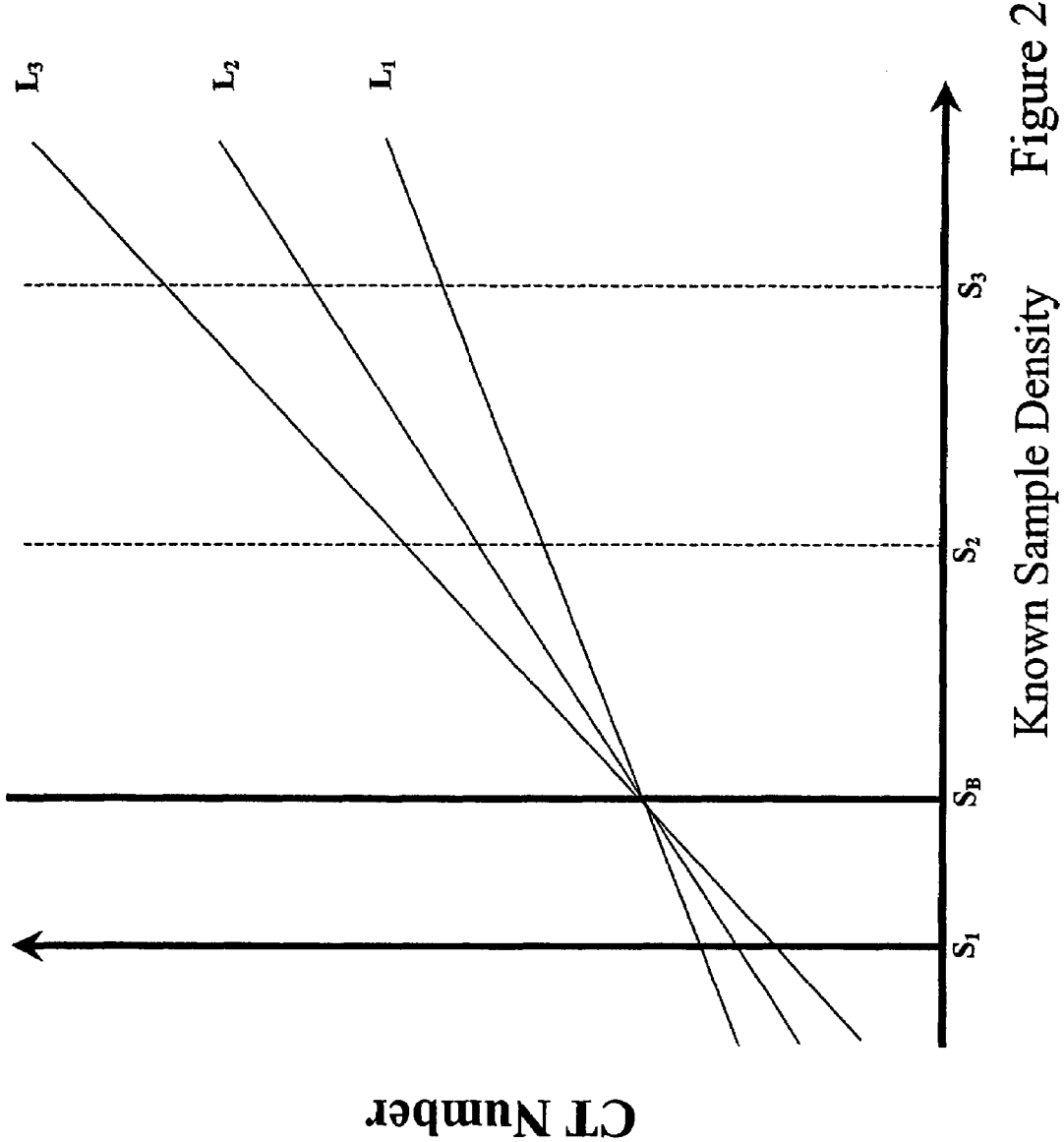
FIG. 2 illustrates hybrid calibration curves at different body locations.

In a step 114, the phantom measurements are expressed in a regression equation of the form $y=I_o+S\times HU_s$. The slope, S, of the regression curves is related to the effective beam energy used to make the image. For different KVps, filtration of the primary beam, and different patient sizes and compositions, the slope will vary. The intercept, $I_o$, of the regression equation is a measure of the CT number of the water density sample. The slope, S, will vary with location in a given patient due to differing amounts and densities of tissue being present in the beam. FIG. 2 is a depiction of three regression equations showing different slopes for 3 regions of the body. These regions could be different cross sectional areas and/or different body compositions of fat, muscle or bone. The regression slope will also vary with CT scanner model and calibration.

The reference tissue region is next located in a step 115. The reference tissue may be blood, the heart filled with blood, subcutaneous fat, internal or external air. Preferably the heart and blood are used in coronary calcium analysis. Other tissue may be preferable in other exams. These tissue regions may be located by making use of their location and expected CT number range and their location relative to the location of the calibration phantom. The operator may place a cursor marker within the reference tissue as a seed point. The software then uses region growing techniques to find the region boundaries.

After either automatic location or manual location, the measuring analysis steps can be applied. One or multiple reference tissues may be used in the calibration. If the reference tissue is the heart and blood, the algorithm identifies the blood filled heart which is surrounded by lung tissue. The location step is aided by first finding the aorta and the inferior margins of the heart, which may be positioned in contact or adjacent to the diaphragm, the liver or both. The operator may need in some cases to place a cursor marker to aid in this boundary distinction.

In a step 116, the regression equation is applied to the entire image, or, in some cases, may be applied to only the reference tissue region plus additional surrounding tissue. This step provides an improved definition of the reference tissue boundaries. Alternatively, the regression equation may not be applied to the image or reference tissue region. The methodology will work without this optional step.

In a step 117, the regression equation is used to define a quantitative value as the specific edge. By using calibration, the boundaries of the reference tissue can be reproducibly located and relocated with fixed criteria. This edge definition and calibration is not to be confused with the calibration step which defines the edge of the target tissue that will be discussed below.

Figure 3:
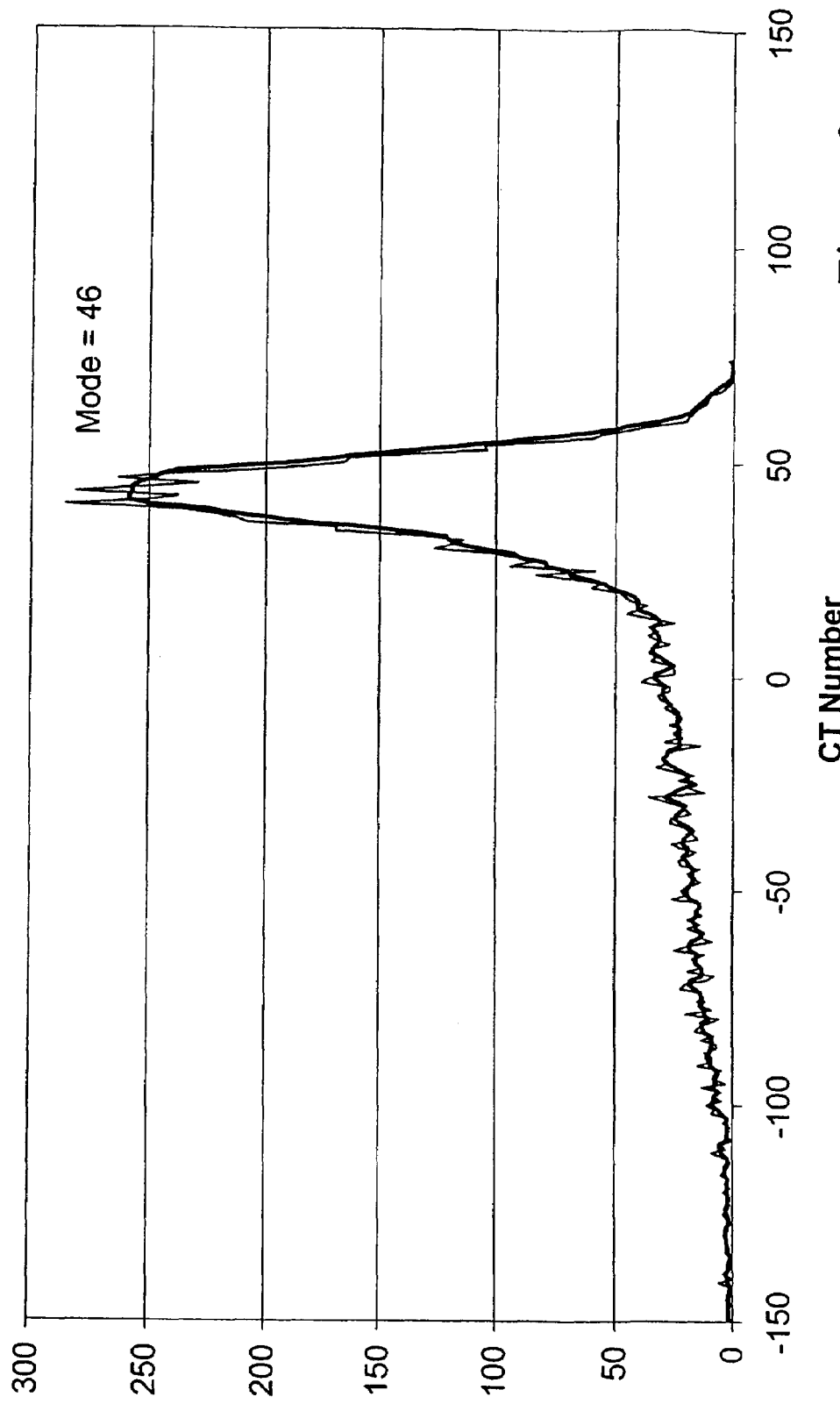
FIG. 3 illustrates a histogram of the HU values of the segmented heart volume showing the mode which is used for the calibration method of the present invention.

The voxels within the boundaries of the reference tissue are next used to calculate a histogram in a step 118. A representative histogram of the heart as reference tissue is shown in FIG. 3.

The histogram is smoothed and a Gaussian curve is fit to the peak. Several neighboring slices may be scanned at this point in a step 119. The ends of the histogram may be filtered to remove unwanted voxel readings not representative of blood. Then, in a step 120, a background level due to scattered radiation or surrounding tissue, which can be distinguished from the reference tissue, may be subtracted. FIG. 5 shows changes in scattered radiation outside and adjacent to the body. ROIs were positioned in air and the histogram plotted of the pixel values of the ROI. With correct air calibration and no scattered radiation, the ROI should produce HU values around −1000. The mode of the plots produce values of −964, −980, −987 and −994. These measurements show differences from expected values of 6 to 36 HU, which differences depend on location. Similar measurements can be made on air within the body.

The mode of the Gaussian fit is next calculated in a step 121. The calculated mode is next combined with the phantom regression equation to create the final hybrid calibration equation in a step 122. The calibration equation is an expression of the form:

$$T_d=(HU_b-HU'_b)+S\times HU,$$

where $T_d$ is the tissue density of the target tissue or organ to be analyzed. $T_d$ may be expressed as corrected HU values or $T_d$ may be represented in tissue density units such as grams per cubic centimeter (g/cc). $HU_b$ is the previously determined or known CT number of representative blood, i.e., the known blood density or HU values of blood determined in vitro under similar scanning conditions. Blood samples from representative patients are placed in a container and scanned inside a tissue-like phantom, while maintaining temperatures representative of the human body, and scanning conditions representative of the clinical scans. $HU'_b$ is the measured reference tissue density which in this example, is the mode of the histogram of the heart and blood. S is the slope of the regression equation measured from the calibration phantom samples. HU is the scanner CT number or may be a CT number measure of the target tissue to be analyzed. Note that the target tissue may be coronary calcifications, an organ, an unknown mass, the edge of a target region or organ. Alternatively, the hybrid calibration can be applied to the entire image, thus creating a new calibrated image where all image voxels are calibrated to the hybrid reference in a step 123.

After the image is calibrated, the target tissue or detail to be analyzed is next located in a step 124. The target tissue may be located by search algorithms which make use of location, density and shape of the targets. In one embodiment, the target tissue is located by using the known phantom location to set a search ROI in which a more detailed search occurs. Lung calcifications can be found by prior art methods, such as described in U.S. Pat. No. 4,922,915, cited above. Using the location of the vertebral body, the abdominal aorta can be located within an ROI which includes the aorta. The measurement ROI may then be placed around the blood of the aorta and the calcifications in the aorta.

CT images often have streak artifacts, particularly in fast CT scans of the heart, which makes it difficult to detect small details such as calcifications. A low pass filter can be applied to the image in a step 125 to reduce the streak artifacts without affecting the target details, such as the small calcifications in this example.

When the target tissue is located and the image calibrated, a pre-selected and quantitative threshold is applied or a quantitative threshold is defined as the edge of a region in a step 126. The edge of a target or threshold value is located in a step 127 to enable reproducible quantitative measurements of dimensions, volumes or mass in a step 128. FIG. 4A shows a depiction of an image detail, for example, a round blood vessel. When the detail is imaged in, for example, a CT scanner, the final image may have 12 or more bits of gray scale values. All of the gray scale values can not be displayed at one time on a monitor, and further, the eye can not see this many gray levels. The image is therefore displayed with windows (number of gray levels) and levels (the central gray level of the window). A variety of windows and levels are possible in a relatively continuous process. FIG. 4 shows a depiction of an image detail and the voxel intensities across the detail. A plot across the image would produce the scan line of FIG. 4, showing the scan profile with edges. If the image is displayed on an electronic monitor or filmed, the perceived location of the edges to the eye will vary with window and level.

FIG. 4 also shows how the apparent location of the detail edges changes with display level. When the display level is changed from $L_1$ to $L_2$, the apparent or measured width (distance) increases from $D_1$ to $D_2$. As a result, if the level is changed, the object appears to get larger and will be perceived as larger by the observer. If physical measurements are made of the size or boundaries of the details, they will change, also based on the display settings. If the edge is calibrated as disclosed herein, and a quantitative edge defined, the detail can be reproducibly measured and displayed.

With a defined quantitative threshold or a defined edge parameter or both, the boundaries of a target tissue or the number of voxels or both that meet the threshold criteria can be determined accurately. The number of voxels satisfying the threshold or the extent of the target details can be summed for neighboring CT slices to create a calcium score which has 3D definition under the quantitative threshold. The calibrated image and a defined threshold enables reproducible detection without operator location of details, such as calcifications within the heart or the aorta. Multiple details within a CT slice or the volume can be analyzed by repeating the steps 110-128, as illustrated by a step 129.

Figure 7:
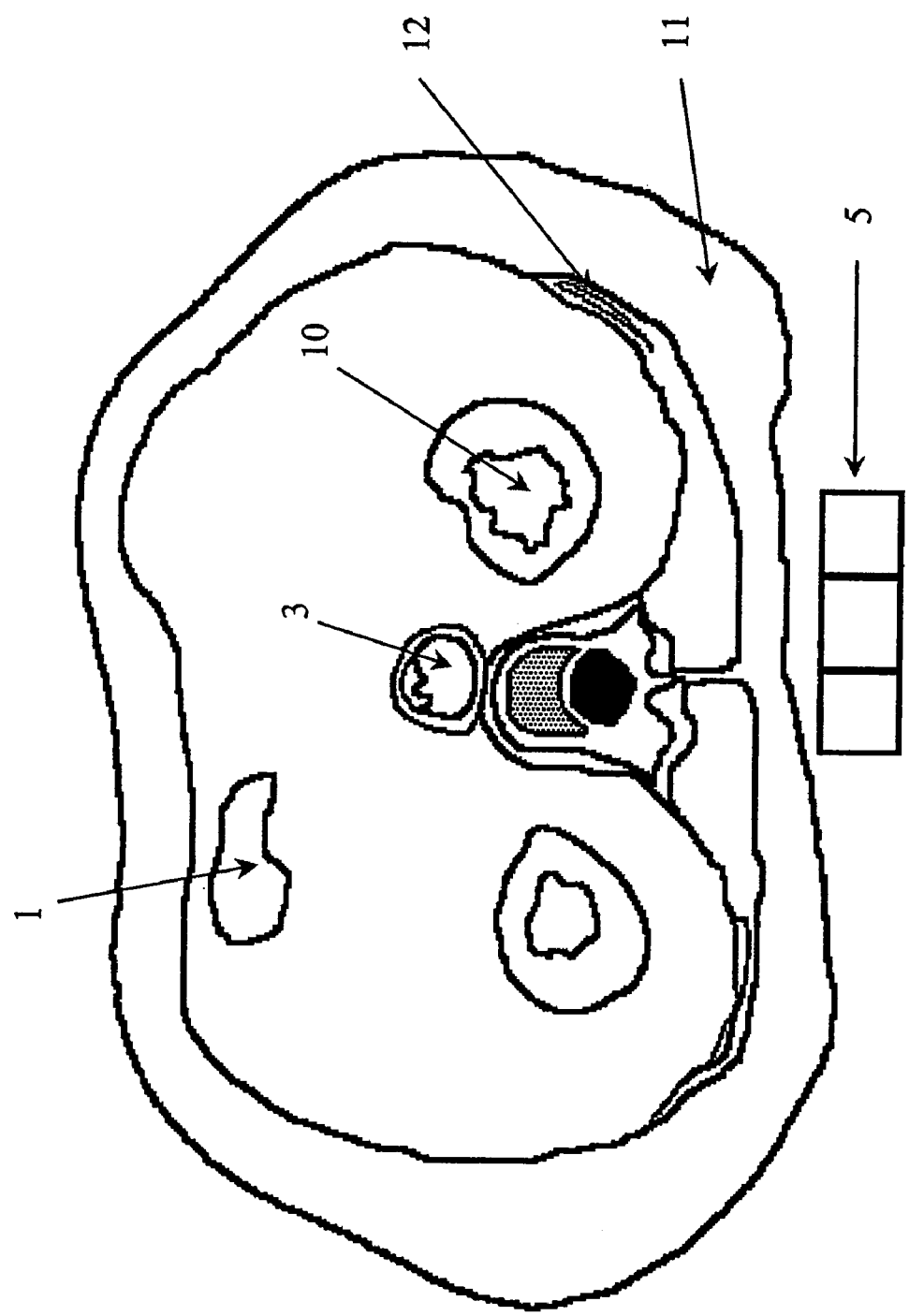
FIG. 7 illustrates a cross sectional image of the abdomen with reference calibration phantom in place.

Calcifications may be detected and quantified in other parts of the body, for example, the abdominal aorta. FIG. 7 shows a cross sectional image of the abdomen with the reference calibration phantom 5 in place. The abdominal aorta shows a calcified plaque 3. The kidneys 10 and the abdominal muscle 12 are also seen. Bowel gas 1 is also shown at essentially air density. The subcutaneous fat 11 is relatively homogeneous and is distributed around the circumference of the body. The subcutaneous fat provides a sharp contrast with the surrounding air. The muscle wall can be segmented out from the fat to define a 360° region of purely subcutaneous fat.

The results of the foregoing method are reported as a parameter, such as mass, volume, or a calibrated calcium score in the case of calcium analysis in the coronary arteries or aorta.

The foregoing calibration procedure can be used with lesser performance on images without the calibration phantom, or with an alternative phantom made of alternative materials. A variety of plastics simulating muscle or fat may be used as the phantom samples. The use of hybrid calibration is therefore not limited to a particular reference phantom or a particular way of being used, i.e., simultaneously scanned versus independent scanning.

The calibration method of the current disclosure may also be used with subcutaneous fat or internal air as a calibration reference for the hybrid method. One skilled in the art can see that such alternative methods fall within the slope of the following claims.

This invention may be embodied in other specific forms without departing from the essential characteristics as described herein. The embodiments described above are to be considered in all respects as illustrative only and not restrictive in any manner. The scope of the invention is indicated by the following claims rather than by the foregoing description. Any and all changes which come within the meaning and range of equivalency of the claims are to be considered within their scope.

What is claimed is:

1. A method of determining tissue densities from computed tomography (CT) images, the images containing voxel representations of x-ray attenuation of a subject's body, the method comprising:
   acquiring at least one CT image of the subject's body;
   determining a CT attenuation measure of at least one region of a calibration phantom;
   locating a region of the image representing the subject's blood or heart tissue;
   determining a CT attenuation measure of at least one region representing blood or heart tissue;
   combining the CT measure of the phantom and the CT measure of the blood or heart tissue to develop a calibration relationship;
   applying the calibration relationship to the image of the subject's body; and
   recording a calibrated image.

2. The method of claim 1, wherein the CT attenuation measure of the region representing blood or heart tissue is the mode of a histogram of CT numbers representing x-ray attenuation of the region.

3. The method of claim 1, wherein the CT attenuation measure of the region representing blood or heart tissue is a mean of CT numbers representing x-ray attenuation of the region.

4. The method of claim 1, wherein the calibration relationship is a regression equation.

5. The method of claim 1, wherein the calibrated image contains representations of voxels expressed in density units.

6. A method displaying a calibrated CT image of a subject, the method comprising:
   imaging a subject to produce an image;
   imaging a reference material having a known property other than x-ray attenuation;
   calibrating the image of the subject by calibrating pixel values of the image based on pixel values of the reference material;
   defining image display gray ranges of window and level for the calibrated image of the subject; and
   displaying the calibrated image of the subject with the defined display gray ranges.

7. The method of claim 6, wherein the known reference is an external phantom.

8. The method of claim 6, wherein the known reference is an internal tissue of the subject.

9. The method of claim 6, wherein the display gray scale ranges are expressed in HU values.

10. The method of claim 6, wherein the display gray ranges are expressed in density units.

11. The method of claim 10, wherein the density units comprise grams per cubic centimeter.

12. A method of determining tissue densities from computed tomography (CT) images, the images containing voxel representations of x-ray attenuation of a subject's body, the method comprising:
   acquiring at least one CT image of the subject's body and a calibration phantom;

determining a CT attenuation measure of at least one region of the phantom;

identifying a region of the image containing the subject's muscle tissue;

determining a CT attenuation measure of at least one region containing muscle tissue;

combining the CT attenuation measure of the phantom and the CT measure of the muscle to develop a calibration relationship; and applying the calibration relationship to the image.

13. The method of claim 12, wherein the CT attenuation measure of the at least one region containing muscle tissue is the mode of a histogram of the CT numbers of the region.

14. The method of claim 12, wherein the CT attenuation measure of the at least one region containing muscle tissue is the mean of the CT numbers of the region.

15. The method of claim 12, wherein the calibrated image contains voxels expressed in density units.

16. A method to calibrate a computed tomography image of a subject, the method comprising:

imaging a reference calibration material with known physical properties;

imaging the subject under similar imaging conditions;

identifying a region of tissue of the subject with known properties;

determining a CT attenuation measure of voxels of the known tissue within at least one region of the subject;

determining a calibration relationship which includes a measure of CT attenuation in the calibration material and which includes a relationship determined from the CT attenuation measure of the known tissue related to known properties of the known tissue; and applying the calibration relationship to the image to create a modified image with improved properties.

17. The method of claim 16, wherein the known tissue is muscle or muscle/blood of the subject.

18. The method of claim 16, wherein the known tissue is fat.

19. The method of claim 16, wherein the best measure is the mode of a histogram of the CT attenuations in the at least one region of tissue with known properties.

20. A method of displaying an image of a subject, the image containing gray scale pixel values representative of tissue properties of the subject, the method comprising:

imaging the subject to produce an image with gray scale pixel values representative of tissue properties of the subject;

imaging a reference material with known properties;

calibrating the pixel values of the image with pixel values of the reference material;

defining image display gray ranges of window and level, which are known in units of the known properties of the reference material; and displaying the image of the subject with gray scale pixel value determined from the relationship of the known properties of the reference material and the pixel values of the image.

21. The method of claim 20, wherein the reference material with known properties is an external phantom.

22. The method of claim 20, wherein the reference material with known properties is an internal tissue of the subject.

23. The method of claim 20, wherein the imaging is magnetic resonance imaging.

24. The method of claim 20, wherein the display gray scale ranges are calibrated in grams per cc.

25. The method of claim 20, wherein the display gray scale is expressed in physical units where 1 g per cc is referenced to 0 on a density gray scale.

* * * * *